(12) United States Patent
Frevert et al.

(10) Patent No.: US 8,912,140 B2
(45) Date of Patent: *Dec. 16, 2014

(54) PEGYLATED MUTATED CLOSTRIDIUM BOTULINUM TOXIN

(71) Applicant: Merz Pharma GmbH & Co. KGaA, Frankfurt am Main (DE)

(72) Inventors: Jürgen Frevert, Berlin (DE); Volker Specht, Berlin (DE)

(73) Assignee: Merz Pharma GmbH & Co. KGaA, Frankfurt Au Main (DE)

( * ) Notice: Subject to any disclaimer, the term of this patent is extended or adjusted under 35 U.S.C. 154(b) by 119 days.

This patent is subject to a terminal disclaimer.

(21) Appl. No.: 13/624,493

(22) Filed: Sep. 21, 2012

(65) Prior Publication Data

US 2013/0156747 A1 Jun. 20, 2013

Related U.S. Application Data

(62) Division of application No. 13/185,925, filed on Jul. 19, 2011, now Pat. No. 8,298,550, which is a division of application No. 12/282,601, filed as application No. PCT/EP2007/002296 on Mar. 15, 2007, now Pat. No. 8,003,601.

(30) Foreign Application Priority Data

Mar. 15, 2006 (EP) .................................. 06005300

(51) Int. Cl.
| | | |
|---|---|---|
| *A61K 38/00* | (2006.01) | |
| *A61K 39/00* | (2006.01) | |
| *C07K 1/00* | (2006.01) | |
| *C12N 9/96* | (2006.01) | |
| *C07K 14/33* | (2006.01) | |

(52) U.S. Cl.
CPC .. *C12N 9/96* (2013.01); *C07K 14/33* (2013.01)
USPC .......................... 514/2.1; 530/350; 424/184.1

(58) Field of Classification Search
None
See application file for complete search history.

(56) References Cited

U.S. PATENT DOCUMENTS

| | | | | |
|---|---|---|---|---|
| 8,003,601 | B2 * | 8/2011 | Frevert et al. .................. | 514/2.1 |
| 2002/0197278 | A1 | 12/2002 | Allison ....................... | 424/239.1 |
| 2003/0027752 | A1 | 2/2003 | Steward et al. ................ | 514/12 |

FOREIGN PATENT DOCUMENTS

| | | |
|---|---|---|
| WO | WO 00/74703 | 12/2000 |
| WO | WO 03/000193 | 1/2003 |
| WO | WO 2006/026780 | 3/2006 |

OTHER PUBLICATIONS

Bavari et al., "Identifying the principal protective antigenic determinants of type A botulinum neurotoxin," *Vaccine*, 16(19):1850-1856, 1998.
Ford et al., "Fusion tails for the recovery and purification of recombinant proteins," *Protein Expression and Purification*, 2:95-107, 1991.
Lacy et al., "Crystal structure of botulinum neurotoxin type A and implications for toxicity," *Nat. Struct. Biol.* 5:898-902, 1998.
Office Communication issued in U.S. Appl. No. 12/282,601, dated Jan. 10, 2011.
Office Communication issued in U.S. Appl. No. 12/282,601, dated Nov. 22, 2010.
Office Communication issued in U.S. Appl. No. 13/185,925, dated Jun. 13, 2012.
Schantz et al., "Properties and use of botulinum toxin and other microbial neurotoxins in medicine," *Microbiological Reviews*, 56(1): 80-99, 1992.
Swaninathan et al., "Structural analysis of the catalytic and binding sites of *Clostridium botulinum* neurotoxin B," *Nat. Struct. Biol.*, 7:693-699, 2000.

\* cited by examiner

*Primary Examiner* — Albert Navarro
(74) *Attorney, Agent, or Firm* — Parker Highlander PLLC

(57) ABSTRACT

The invention relates to a modified botulinum toxin comprising a natural heavy chain and a modified light chain, characterized in that the modification of the light chain resides in that it comprises (i) an extension of the chain on its N-terminus which has the structure —$(C)_n$-$(tag)_m$-$(X)_l$— in the direction from the N- to the C-terminal end, wherein C represents a cysteine residue, tag represents any tag and X represents the residue of any naturally occurring amino acid, n represents an integer from 1 to 50, m represents 0 or 1, and l represents 0 or an integer from 1 to 50, and in that (ii) at least one of the cysteine residues in the extension of the chain is coupled to at least one chain of PEG.

8 Claims, 6 Drawing Sheets

FIG. 1

SEQ ID NO: 1: BoNT/A-L/For    ACCACTCCATGGCATTTGTTAATAAACAATTTAAT

Figure 2:
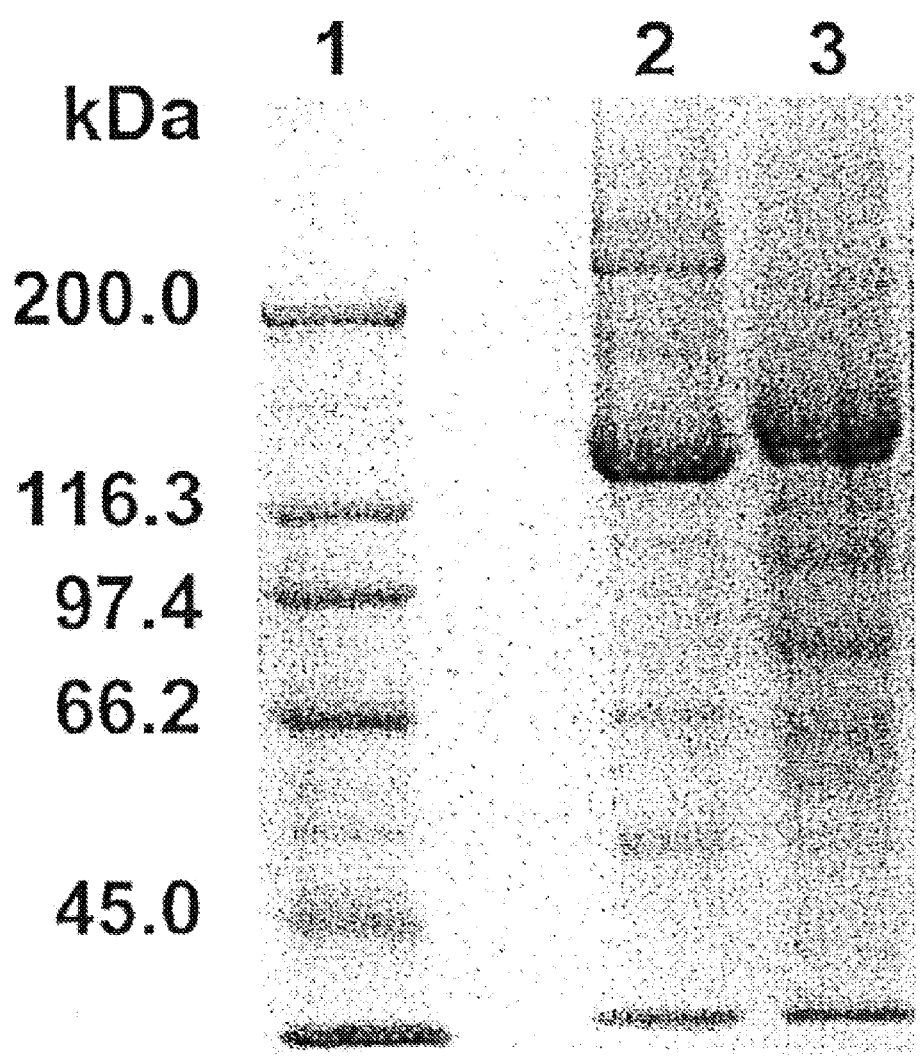

SEQ ID NO: 2: BoNT/A-L/Re    ACCACCAGATCTATTTAAGGCCTTGGATCCACGCG
GAACTAATGATTTAGTTTTAGAAGTTATTATC

SEQ ID NO: 3: BoNT/A-H/For    ACCACCAGGCCTTAAATGATTTATGTATCAAAGTTAA

SEQ ID NO: 4: BoNT/A-H/Rev    ACCACCAGATCTTTACAGTGGCCTTTCTCCCCATCCATC

SEQ ID NO: 5: BoNT(B)-L/For    ACCACTCCATGGCAGTTACAATAAATAATTTTAATTATA

SEQ ID NO: 6: BoNT(B)-L/Rev    ACCACTAGGCCTTGGATCCACGTGGAACCAATGATTTA
GTTTTAGAAGTTATTATCCCACTTTTACACATTTGTATCT
TATATAC

SEQ ID NO: 7: BoNT(B)-H/For    ACCACTAGGCCTCAGGAATATGTATTGATGTTGA

SEQ ID NO: 8: BoNT(B)-H/Rev    ACCACCAGATCTTTATTCAGTCCACCCTTCATC

SEQ ID NO: 9: BoNT(C)-L/For    ACCACTCCATGGCAATAACAATTAACAACTTTAATTATTC

SEQ ID NO: 10: BoNT(C)-L/Rev    GAGAATAGGCCTTGGATCCACGCGGAACTAATGATTTAGT
TTTAGAAGTTATTATCCCTCTATGACAAAATTTTGT

SEQ ID NO: 11: BoNT(C)-H/For    ACCACTAGGCCTTAGATTGTAGAGAGCTTTTAG

SEQ ID NO: 12: BoNT(C)-H/Rev    ACCACCAGATCTTTAAGAAATAAATTTCCAAAAAGATGAA
GTTG

SEQ ID NO: 13: N-C-His/For    GAGGAGAAATTAACTATGGGATGTGGATCGCATCACCATC
AC

SEQ ID NO: 14: N-C-His/Rev
GTGATGGTGATGCGATCCACATCCCATAGTTAATTTCTCCT
C

SEQ ID NO: 15: mutated botulinum neurotoxin type A atgggatgtg gatcgcatca ccatcaccac catcatcacc atcactccat ggcatttgtt aataaacaat ttaattataa agatcctgta aatggtgttg
atattgctta tataaaaatt ccaaatgcag gacaaatgca accagtaaaa gcttttaaaa ttcataataa aatatgggtt
attccagaaa gagatacatt tacaaatcct gaagaaggag atttaaatcc accaccagaa gcaaaacaag ttccagtttc atattatgat tcaacatatt
taagtacaga taatgaaaaa gataattatt taaagggagt tacaaaatta tttgagagaa tttattcaac tgatcttgga

FIG. 1 (Cont'd)

agaatgttgt taacatcaat agtaagggga ataccatttt ggggtggaag tacaatagat acagaattaa aagttattga tactaattgt attaatgtga
tacaaccaga tggtagttat agatcagaag aacttaatct agtaataata ggaccctcag ctgatattat acagtttgaa
tgtaaaagct ttggacatga agttttgaat cttacgcgaa atggttatgg ctctactcaa tacattagat ttagcccaga ttttacattt
ggttttgagg agtcacttga agttgataca aatcctcttt taggtgcagg caaatttgct acagatccag cagtaacatt agcacatgaa cttatacatg
ctggacatag attatatgga atagcaatta atccaaatag ggttttaaa gtaaatacta atgcctatta tgaaatgagt
gggttagaag taagctttga ggaacttaga acatttgggg gacatgatgc aaagtttata gatagtttac aggaaaacga atttcgtcta
tattattata ataagtttaa agatatagca agtacactta ataaagctaa atcaatagta ggtactactg cttcattaca gtatatgaaa
aatgttttta aagagaaata tctcctatct gaagatacat ctggaaaatt ttcggtagat aaattaaaat ttgataagtt atacaaaatg
ttaacagaga tttacacaga ggataatttt gttaagtttt ttaaagtact taacagaaaa acatatttga attttgataa agccgtattt
aagataaaata tagtacctaa ggtaaattac acaatatatg atggatttaa tttaagaaat acaaatttag cagcaaactt taatggtcaa
aatacagaaa ttaataatat gaattttact aaactaaaaa attttactgg attgtttgaa ttttataagt tgctatgtgt aagagggata
ataacttcta aaactaaatc attagttccg cgtggatcca aggcctttaaa tgattatgt atcaaagtta ataattggga cttgtttttt
agtccttcag aagataattt tactaatgat ctaaataaag gagaagaaat tacatctgat actaatatag aagcagcaga agaaaatatt agtttagatt
taatacaaca atattattta acctttaatt ttgataatga acctgaaaat atttcaatag aaaatctttc aagtgacatt
ataggccaat tagaacttat gcctaatata gaaagatttc ctaatggaaa aaagtatgag ttagataaat atactatgtt ccattatctt
cgtgctcaag aatttgaaca tggtaaatct aggattgctt taacaaaatc tgttaacgaa gcattattaa atcctagtcg tgttatacata
ttttttttctt cagactatgt aaagaaagtt aataaagcta cggaggcagc tatgttttta ggctgggtag aacaattagt atatgatttt
accgatgaaa ctagcgaagt aagtactacg gataaaattg cggatataac tataattatt ccatatatag gacctgcttt aaatataggt
aatatgttat ataaagatga ttttgtaggt gctttaatat tttcaggagc tgttatctg ttagaattta taccagagat tgcaatacct
gtattaggta cttttgcact tgtatcatat attgcgaata aggttctaac cgttcaaaca atagataatg cttaagtaa aagaaatgaa
aaatgggatg aggtctataa atatatagta acaaattggt tagcaaaggt taatacacag attgatctaa taagaaaaaa aatgaaagaa gctttagaaa
atcaagcaga agcaacaaag gctataataa actatcagta taatcaatat actgaggaag agaaaaataa tattaatttt
aatattgatg atttaagttc gaaacttaat gagtctataa ataaagctat gattaatata aataaatttt tgaatcaatg ctctgtttca
tatttaatga attctatgat ccctatggt gttaaacggt tagaagattt tgatgctagt cttaaagatg cattattaaa gtatatatat
gataatagag gaacttttaat tggtcaagta gatagattaa aagataaagt taataataca cttagtacag atataccttt tcagcttttcc
aaatacgtag ataatcaaag attattatct acatttactg aatatattaa gaatatatt aatactcta tattgaattt aagatatgaa
agtaatcatt taatagactt atctaggtat gcatcaaaaa taaatattgg tagtaaagta aattttgatc caatagataa aaatcaaatt
caattattta atttagaaag tagtaaaatt gaggtaattt taaaaaatgc tattgtatat aatagtatgt atgaaaattt tagtactagc
ttttggataa gaattcctaa gtatttaac agtataagtc taaataatga atatacaata ataaattgta tggaaaataa ttcaggatgg
aaagtatcac ttaattatgg tgaaataatc tggactttac aggatactca ggaaataaaa caaagagtag tttttaaata cagtcaaatg
attaatatat cagattatat aaacagatgg attttttgtaa ctatccactaa taatagatta aataactcta aaatttatat aaatggaaga
ttaatagatc aaaaaccaat ttcaaattta ggtaatattc atgctagtaa taatataatg tttaaattag atggttgtag agatacacat
agatatattt ggataaaata ttttaatctt tttgataagg aattaaatga aaaagaaatc aaagatttat atgataatca atcaaattca
ggtatttaa aagactttg gggtgattat ttacaatatg ataaaccata ctatatgtta aatttatatg atccaaataa atatgtcgat
gtaaataatg taggtattag aggttatatg tatcttaaag ggcctagagg tagcgtaatg actacaaaca tttatttaaa ttcaagtttg
tatagggga caaaatttat tataaaaaaa tatgcttctg gaaataaaga taatattgt agaaataatg atcgtgtata tattaatgta
gtagttaaaa ataaagaata taggttagct actaatgcat cacaggcagg cgtagaaaaa atactaagtg cattagaaat acctgatgta ggaaatctaa
gtcaagtagt agtaatgaag tcaaaaaatg atcaaggaat aacaaataaa tgcaaaatga atttacaaga taataatggg
aatgatatag gcttttatagg atttcatcag ttaataata tagctaaact agtagcaagt aattggtata atagacaaat agaaagatct
agtaggact tgggttgctc atgggaattt attcctgtag atgatggatg gggagaaagg ccactgtaa

FIG. 1 (Cont'd)

SEQ ID NO: 16: mutated botulinum neurotoxin typeA

Met Gly Cys Gly Ser His His His His His His His His His Ser Met Ala Phe Val Asn

Lys Gln Phe Asn Tyr Lys Asp Pro Val Asn Gly Val Asp Ile Ala Tyr Ile Lys Ile Pro Asn

Val Gly Gln Met Gln Pro Val Lys Ala Phe Lys Ile His Asn Lys Ile Trp Val Ile Pro Glu

Arg Asp Thr Phe Thr Asn Pro Glu Glu Gly Asp Leu Asn Pro Pro Glu Ala Lys Gln Val

Pro Val Ser Tyr Tyr Asp Ser Thr Tyr Leu Ser Thr Asp Asn Glu Lys Asp Asn Tyr Leu Lys

Gly Val Thr Lys Leu Phe Glu Arg Ile Tyr Ser Thr Asp Leu Gly Arg Met Leu Leu Thr Ser

Ile Val Arg Gly Ile Pro Phe Trp Gly Gly Ser Thr Ile Asp Thr Glu Leu Lys Val Ile Asp Thr

Asn Cys Ile Asn Val Ile Gln Pro Asp Gly Ser Tyr Arg Ser Glu Glu Leu Asn Leu Val Ile Ile

Gly Pro Ser Ala Asp Ile Ile Gln Phe Glu Cys Lys Ser Phe Gly His Glu Val Leu Asn Leu Thr

Arg Asn Gly Tyr Gly Ser Thr Gln Tyr Ile Arg Phe Ser Pro Asp Phe Thr Phe Gly Phe Glu Glu

Ser Leu Glu Val Asp Thr Asn Pro Leu Leu Gly Ala Gly Lys Phe Ala Thr Asp Pro Ala Val Thr

Leu Ala His Glu Leu Ile His Ala Gly His Arg Leu Tyr Gly Ile Ala Ile Asn Pro Asn Arg Val Phe

Lys Val Asn Thr Asn Ala Tyr Tyr Glu Met Ser Gly Leu Glu Val Ser Phe Glu Glu Leu Arg Thr

Phe Gly Gly His Asp Ala Lys Phe Ile Asp Ser Leu Gln Glu Asn Glu Phe Arg Leu Tyr Tyr Tyr

Asn Lys Phe Lys Asp Ile Ala Ser Thr Leu Asn Lys Ala Lys Ser Ile Val Gly Thr Thr Ala Ser Leu

Gln Tyr Met Lys Asn Val Phe Lys Glu Lys Tyr Leu Leu Ser Glu Asp Thr Ser Gly Lys Phe Ser Val

Asp Lys Leu Lys Phe Asp Lys Leu Tyr Lys Met Leu Thr Glu Ile Tyr Thr Glu Asp Asn Phe Val Lys

Phe Phe Lys Val Leu Asn Arg Lys Thr Tyr Leu Asn Phe Asp Lys Ala Val Phe Lys Ile Asn Ile Val

Pro Lys Val Asn Tyr Thr Ile Tyr Asp Gly Phe Asn Leu Arg Asn Thr Asn Leu Ala Ala Asn Phe Asn

Gly Gln Asn Thr Glu Ile Asn Asn Met Asn Phe Thr Lys Leu Lys Asn Phe Thr Gly Leu Phe Glu Phe

FIG. 1 (Cont'd)

Tyr Lys Leu Leu Cys Val Arg Gly Ile Ile Thr Ser Lys Thr Lys Ser Leu Val Pro Arg Gly Ser Lys Ala

Leu Asn Asp Leu Cys Ile Lys Val Asn Asn Trp Asp Leu Phe Phe Ser Pro Ser Glu Asp Asn Phe Thr

Asn Asp Leu Asn Lys Gly Glu Glu Ile Thr Ser Asp Thr Asn Ile Glu Ala Ala Glu Glu Asn Ile Ser Leu

Asp Leu Ile Gln Gln Tyr Tyr Leu Thr Phe Asn Phe Asp Asn Glu Pro Glu Asn Ile Ser Ile Glu Asn Leu

Ser Ser Asp Ile Ile Gly Gln Leu Glu Leu Met Pro Asn Ile Glu Arg Phe Pro Asn Gly Lys Lys Tyr Glu

Leu Asp Lys Tyr Thr Met Phe His Tyr Leu Arg Ala Gln Glu Phe Glu His Gly Lys Ser Arg Ile Ala Leu

Thr Asn Ser Val Asn Glu Ala Leu Leu Asn Pro Ser Arg Val Tyr Thr Phe Phe Ser Ser Asp Tyr Val Lys

Lys Val Asn Lys Ala Thr Glu Ala Ala Met Phe Leu Gly Trp Val Glu Gln Leu Val Tyr Asp Phe Thr

Asp Glu Thr Ser Glu Val Ser Thr Thr Asp Lys Ile Ala Asp Ile Thr Ile Ile Ile Pro Tyr Ile Gly Pro Ala

Leu Asn Ile Gly Asn Met Leu Tyr Lys Asp Asp Phe Val Gly Ala Leu Ile Phe Ser Gly Ala Val Ile Leu

Leu Glu Phe Ile Pro Glu Ile Ala Ile Pro Val Leu Gly Thr Phe Ala Leu Val Ser Tyr Ile Ala Asn Lys

Val Leu Thr Val Gln Thr Ile Asp Asn Ala Leu Ser Lys Arg Asn Glu Lys Trp Asp Glu Val Tyr Lys

Tyr Ile Val Thr Asn Trp Leu Ala Lys Val Asn Thr Gln Ile Asp Leu Ile Arg Lys Lys Met Lys Glu Ala

Leu Glu Asn Gln Ala Glu Ala Thr Lys Ala Ile Ile Asn Tyr Gln Tyr Asn Gln Tyr Thr Glu Glu Glu Lys

Asn Asn Ile Asn Phe Asn Ile Asp Asp Leu Ser Ser Lys Leu Asn Glu Ser Ile Asn Lys Ala Met Ile Asn

Ile Asn Lys Phe Leu Asn Gln Cys Ser Val Ser Tyr Leu Met Asn Ser Met Ile Pro Tyr Gly Val Lys Arg

Leu Glu Asp Phe Asp Ala Ser Leu Lys Asp Ala Leu Leu Lys Tyr Ile Tyr Asp Asn Arg Gly Thr Leu Ile

Gly Gln Val Asp Arg Leu Lys Asp Lys Val Asn Asn Thr Leu Ser Thr Asp Ile Pro Phe Gln Leu Ser Lys

Tyr Val Asp Asn Gln Arg Leu Leu Ser Thr Phe Thr Glu Tyr Ile Lys Asn Ile Ile Asn Thr Ser Ile Leu Asn

Leu Arg Tyr Glu Ser Asn His Leu Ile Asp Leu Ser Arg Tyr Ala Ser Lys Ile Asn Ile Gly Ser Lys Val Asn

Phe Asp Pro Ile Asp Lys Asn Gln Ile Gln Leu Phe Asn Leu Glu Ser Ser Lys Ile Glu Val Ile Leu Lys Asn

FIG. 1 (Cont'd)

Ala Ile Val Tyr Asn Ser Met Tyr Glu Asn Phe Ser Thr Ser Phe Trp Ile Arg Ile Pro Lys Tyr Phe Asn Ser

Ile Ser Leu Asn Asn Glu Tyr Thr Ile Ile Asn Cys Met Glu Asn Asn Ser Gly Trp Lys Val Ser Leu Asn Tyr

Gly Glu Ile Ile Trp Thr Leu Gln Asp Thr Gln Glu Ile Lys Gln Arg Val Val Phe Lys Tyr Ser Gln Met

Ile Asn Ile Ser Asp Tyr Ile Asn Arg Trp Ile Phe Val Thr Ile Thr Asn Asn Arg Leu Asn Asn Ser Lys Ile

Tyr Ile Asn Gly Arg Leu Ile Asp Gln Lys Pro Ile Ser Asn Leu Gly Asn Ile His Ala Ser Asn Asn Ile

Met Phe Lys Leu Asp Gly Cys Arg Asp Thr His Arg Tyr Ile Trp Ile Lys Tyr Phe Asn Leu Phe Asp

Lys Glu Leu Asn Glu Lys Glu Ile Lys Asp Leu Tyr Asp Asn Gln Ser Asn Ser Gly Ile Leu Lys Asp

Phe Trp Gly Asp Tyr Leu Gln Tyr Asp Lys Pro Tyr Tyr Met Leu Asn Leu Tyr Asp Pro Asn Lys Tyr

Val Asp Val Asn Asn Val Gly Ile Arg Gly Tyr Met Tyr Leu Lys Gly Pro Arg Gly Ser Val Met Thr Thr

Asn Ile Tyr Leu Asn Ser Ser Leu Tyr Arg Gly Thr Lys Phe Ile Ile Lys Lys Tyr Ala Ser Gly Asn Lys

Asp Asn Ile Val Arg Asn Asn Asp Arg Val Tyr Ile Asn Val Val Val Lys Asn Lys Glu Tyr Arg Leu

Ala Thr Asn Ala Ser Gln Ala Gly Val Glu Lys Ile Leu Ser Ala Leu Glu Ile Pro Asp Val Gly Asn

Leu Ser Gln Val Val Val Met Lys Ser Lys Asn Asp Gln Gly Ile Thr Asn Lys Cys Lys Met Asn Leu

Gln Asp Asn Asn Gly Asn Asp Ile Gly Phe Ile Gly Phe His Gln Phe Asn Asn Ile Ala Lys Leu Val

Ala Ser Asn Trp Tyr Asn Arg Gln Ile Glu Arg Ser Ser Arg Thr Leu Gly Cys Ser Trp Glu Phe Ile

Pro Val Asp Asp Gly Trp Gly Glu Arg Pro Leu

PEGYLATED MUTATED CLOSTRIDIUM BOTULINUM TOXIN

This application is a divisional of U.S. application Ser. No. 13/185,925 filed Jul. 19, 2011, which is a divisional of U.S. application Ser. No. 12/282,601, now U.S. Pat. No. 8,003,601, filed as a national phase application under 35 U.S.C. §371 of International Application No. PCT/EP2007/002296 filed Mar. 15, 2007, which claims priority to European Patent Application No. EP 06 005 300.6 filed Mar. 15, 2006. The entire text of each of the above referenced disclosures is specifically incorporated herein by reference without disclaimer.

The present invention relates to modified botulinum toxins (BoNT), which have enhanced stability and thus a prolonged therapeutic duration of action as compared to the corresponding native botulinum toxins. Furthermore, the present invention relates to pharmaceutical compositions comprising these modified botulinum toxins. Finally the present invention relates to nucleic acids, which encode these modified botulinum toxins.

BACKGROUND OF THE INVENTION

*Clostridium botulinum* is an anaerobically growing, sporulating bacterium, which produces a highly toxic protein. This so-called botulinum toxin is the cause of botulism, a food poisoning, which without the use of intensive care measures can lead to the death of botulism patients. Seven serotypes are distinguished (type A-G, shortly termed BoNT/A, BoNT/B, etc.) that have a similar amino acid sequence, but induce a different antibody response. The toxins (hereinafter also referred to as neurotoxins and botulinum toxins) consist of two functional chains, the light (~50 kDa) and the heavy chain (~100 kDa), which are generated by proteolytic cleavage of the single-chain precursor protein. Other strains do not possess the corresponding protease, therefore the cleavage into the chains takes place in the gastrointestinal tract of the patients (e.g. by trypsin). In the double-chain form the subunits (i.e., the heavy and the light chain) are interconnected via disulfide bridges (for example, in addition there exists an intramolecular disulfide bridge in BoNT/A, i.e., between two cysteine residues of the heavy chain).

Under acidic conditions in vivo the pure neurotoxins do not exist in free form, but form complexes with other clostridial proteins, the so-called (*Clostridium botulinum*) toxin complexes. Different proteins, inter alia with hemagglutinating properties, are involved in these complexes. The composition of the complexes is different between serotypes. The integration into the complex protects the neurotoxin during gastrointestinal passage. These other clostridial proteins (the complexing and complex proteins, respectively) possibly play also a role in the resorption of the neurotoxin. Thus, the incorporation in the complex causes the neurotoxin to be orally bioavailable and to thus constitute a food poison. The target location of the neurotoxins is at the motor endplate, where the muscle is activated by the nerve. The motoneuron releases acetylcholine for activation of the muscle. This release is inhibited by botulinum toxin. The inhibitory effect takes place in 3 sequential steps: binding, translocation, proteolysis. The heavy chain of botulinum toxin binds highly specific to the motoneuron and is subsequently taken up into the nerve cell by endocytosis. Upstream of the binding domain, which is located at the C-terminal end of the heavy chain, there is the translocation domain in the N-terminal portion of the heavy chain, which transports or, rather, facilitates the translocation of the light chain into the cytosol by an as yet unknown mechanism. In the cytosol the light chain becomes active as a protease cleaving highly specific so-called SNARE proteins. The proteolytic specificity of the individual botulinum toxin types is summarized in Table 1. These SNARE proteins are responsible for the fusion of the acetylcholine-loaded secretory vesicles with the cell membrane of the motoneuron. The proteolytic cleavage of one of these SNARE proteins inhibits the formation of a fusion complex and thus further release of acetylcholine. The affected muscle is no longer activated. Previously hyperactive muscles become paralyzed.

TABLE 1

| Botulinum Toxin Type | SNARE protein Substrate of protease activity | Cleavage site in SNARE sequence from rat |
|---|---|---|
| Type A | SNAP 25 | EANQ[197] RATK |
| Type B | VAMP 2 | GASQ[76] FETS |
| Type C | Syntaxin | DTKK[254] AVKY |
|  | SNAP 25 | ANQR[198] ATK |
| Type D | VAMP 2 | RDQK[61] LSED |
| Type E | SNAP 25 | QIDR[180] IMEK |
| Type F | VAMP 2 | ERDQ[60] KLSE |
| Type G | VAMP 2 | ETSA[83] AKLK |

This mechanism of action is taken advantage of in the therapy of a multitude of muscle disorders and spasms, respectively, characterized by an uncontrolled release of acetylcholine (e.g., blepharospasm, torticollis, spasticity) Extremely low amounts of the neurotoxin (in the pg to ng range) are injected in the hyperactive muscle for therapy of dystonia. The neurotoxin diffuses to the motor endplate and reaches the cytosol of the neuron to inhibit the acetylcholine release there. The muscle is paralyzed after 1-2 days.

Various facial wrinkles are formed by cramping of muscles lying beneath the skin, thus also through uncontrolled release of acetylcholine. Botulinum toxins find cosmetic utilization in this context: wrinkles will be removed for about 3 months through injection of extremely low amounts of botulinum toxin.

At present four preparations containing botulinum toxins have received drug-regulatory approval: Botox® (Allergan), Xeomin® (Merz), Dysport® (Ipsen), and NeuroBloc® (Solstice Neurosciences). Botox®, Xeomin®, and Dysport® are lyophilisates of botulinum toxin type A (as complex, neurotoxin and complex, respectively), Botox® and Xeomin® with 100 units per injection vial each, Dysport® with 500 units. NeuroBloc® contains botulinum toxin type B (as complex) with 5,000 and 10,000 units, respectively, in liquid formulation.

Except for NeuroBloc the preparations are available as lyophylisates, which are reconstituted with physiological saline and are injected in the respective muscles in matched doses depending on preparation and indication. The treated muscle will be paralyzed within 48 h. The effect lasts about 3 month, thereafter a further injection must be carried out, if the muscle should remain paralyzed further, i.e. the dystonia is to be treated. Up to now it has not unambiguously elucidated, which processes control the decrease of the effect. As long as the light chain is active as protease, the appropriate SNARE protein is cleaved (e.g., SNAP 25 through the light chain of neurotoxin type A).

Accordingly, the fusion of the secretory vesicles with the plasma membrane and thereby the release of acetylcholine will be inhibited under these conditions, the muscle remains paralyzed. If it were possible to maintain the protease activity of the light chain for an extended time period in the cell, then the duration of action of an appropriate drug would be extended also In contrast to many low molecular active substances active protein substances are characterized by a significantly lower stability. The half life (HL) of some active protein substances in the circulating blood amounts to only a few minutes, so that the (therapeutic) duration of action is strongly restricted and injection must be repeated in short intervals. The HL can be extended, if one is successful in protecting the protein against degradation and elimination processes. One theoretically possible way exists especially for eukaryotic proteins in a higher glycosylation (more carbohydrate moieties) and in adapting the carbohydrate structures to the structures of human glycoproteins, respectively. Another path that has been taken in a series of approved active substances is the coupling of the protein with polyethylene glycol (PEG). PEG can be covalently bonded to the residues of various amino acids, e.g., to lysine (amino function) or cysteine residues (SH function). PEG enhances the molecular weight of the protein without creating immunogenic structures that induce the generation of antibodies to the active substance. To the contrary: the PEGylation reduces the immunogenicity of the active substance. The protein is eliminated more slowly by the increase of the molecular weight and a significant increase in HL is achieved. For maintaining a certain required serum level, the drug has to be injected less often.

PEGylated active protein substances are already processed in some approved drugs (see Table 2). The employment of the partly small proteins (e.g., interferon α 2a:Mr=19.3 kDa) in the original form, i.e. not modified, has shown that the proteins are very rapidly eliminated from the serum. The PEGylation gave rise to a markedly increased molecular weight and thus to a substantially longer half life in the serum. Thus, for example, the serum half life for interferon α 2a is 9 h; PEGylation with a 40 kDa PEG chain drastically increases the molecular weight and extends the half life from 9 to 72 h.

TABLE 2

| Trade name | Starting compound | Coupling of PEG |
|---|---|---|
| Pegasys | interferon α 2a | branched PEG-N-hydroxysuccinimide; Coupling to 4 lysine residues |
| Neulasta | G-CSF | PEG-aldehyde; Coupling to N-terminal methionine |
| Peglutron | interferon α 2b | Succinimidyl carbonate-PEG; Coupling to histidine and lysine residues |
| Somavest | growth hormone antagonist | 4-6 PEG; Coupling to lysine residues and N-terminus |
| Oncaspar | Asparaginase | N-hydroxysuccinimide activated PEG |

However the linkage with one or more PEG chains is subject to restrictions:

1. Preferably the PEG chain diminishes the biological activity of the modified protein (in comparison with the unmodified native protein) not at all or only slightly (in accordance with the invention it is understood that slightly diminished biological activity of the modified protein corresponds to at least 20%, preferably to 30-40% or 50-70% or even to 75-95% of the biological activity of the unmodified native protein). A diminished activity is tolerable in many cases: e.g. the antiviral activity of PEGylated interferon is 25-35% of the non-PEGylated interferon α 2b. PEGylated interferon α 2a even possesses only 1-7% of the activity of the non-PEGylated form.
2. As a multitude of therapeutically employed proteins deploy their activity through the binding to a specific receptor, preferably the PEGylation does not affect, or only slightly affects, the interaction with the receptor (e.g., the interaction can be affected directly by steric hindrance at the binding domain or by alterations of the spatial structure of the protein that have an effect on the binding domain and hence on binding).
3. When the pharmacological effect of the therapeutic protein is (also) mediated through an enzymatic activity (as for instance with asparaginase), preferably the enzymatic activity is not, or only slightly, reduced through the PEGylation.

Preferably the PEGylation of botulinum toxin accomplishes these three criteria. At the same time the modification of the botulinum toxin with PEG preferably influences neither (a) the binding domain of the heavy chain nor (b) the enzymatic activity of the light chain, i.e., the PEG chain preferably does not inhibit the interaction of the catalytic domain from the light chain with the substrate (SNARE Protein). In contrast to other proteases, that cleave short peptides, botulinum toxins require longer peptides as substrates. For instance, a peptide which serves as a substrate for botulinum toxin type B preferably has a sequence of about 40 amino acid residues of the SNARE protein VAMP 2. Peptides with shorter SNARE sequences will also be cleaved, but with substantially lower efficiency. The cleavage domain of the light chain of the botulinum toxin, which has a length comparable to the recognition sequence of about 40 amino acid residues, is preferably not affected by the PEG chain. Moreover, it has to be considered, that besides the cleavage domain responsible for the direct contact of the substrate (SNARE protein and peptide with the SNARE sequence of about 40 amino acid residues, respectively) with the light chain, additional contact sites with sequences on the light chain located distantly to the catalytic domain are needed for optimal activity of botulinum toxin. It has been demonstrated that five additional contact sites for its substrate SNAP 25 are localized on the light chain of botulinum toxin type A: 4 α exosites (AS 102-113, 310-321, 335-348, 351-358) and one β exosite (AS 242-259). Preferably, the contact is not or only marginally impeded through a conjugation of the light chain with PEG. Moreover, the C-terminal part of the heavy chain, the translocation domain, must be operable, i.e., it must ensure that the light chain is transported from the endosomes into the cytosol. This transport process that is absolutely necessary for the action can also be inhibited through the steric hindrance of a PEGylated light chain especially as the translocation domain possibly forms a pore in the endosomal membrane through which a "bulky" PEGylated light chain might not be channeled through.

Coupling of PEG to botulinum toxin is reported in a U.S. patent application (2002/0197278). The coupling serves to diminish the antigenicity and immunogenicity, respectively as well as to enhance the molecular weight for reducing the diffusion. For the selection of the appropriate sites (antigenic determinants) and amino acid residues, respectively, for the PEGylation, reference is being had to the paper of Bavari et al. (Vaccine 16: 1850-1856, 1998). In this paper sequences of the botulinum toxin heavy chain that induce neutralizing antibodies are presented. In the aforementioned patent application it is only stated that (1) the PEGylation should be carried out at, respectively close to one site or at, respectively, close to the sites, which act(s) as an important epitope(s), but which are remote from the catalytic domain (i.e. remote from the light chain) and that (2) PEG may be conjugated to the free terminal carboxy or amino groups or at the amino groups of lysine side chains. (3) As additional alternative for the insertion of PEG into the toxin it is suggested to use the SH groups of naturally occurring or specially inserted cysteine residues; however, the paper advises against this alternative (3), as disulfide bridges between the heavy and the light chain of the botulinum toxin play a role in the spatial configuration of the molecule. There is no example given that discloses the structure of the PEGylated neurotoxin or that discloses on which amino acid residue(s) a PEG molecule of a certain length was attached.

In a further patent application (WO 02/40506) relating to the change in stability, the insertion, the modification or the removal of sites for the in vivo glycosylation, in vivo phosphorylation and primarily the in vivo myristoylation in the botulinum toxin are suggested in order to optionally either enhance or decrease the stability of the botulinum toxin. A whole series of potential modification sites are specified which are located at a significant distance to the N- and C-terminal ends of the neurotoxin light chain. Additional sequences are to be inserted into the polypeptide chain, where carbohydrate chains or phosphate and myristoyl moieties, respectively, are coupled at the light chain by cellular enzymes. Information regarding an accordingly modified neurotoxin or its preparation is however missing.

In a further U.S. patent application (2003/0027752) a peptide residue with a so-called leucine motif (e.g., XEXXXLL) is inserted into the neurotoxin or into the light chain in order to increase the stability of the light chain within the nerve cell. The configuration of the light chain with this motif ensures that it is localized in the vicinity of its substrate at the membrane. Moreover, a so-called "tyrosine based motif" (YXXHy, Y=tyrosine, Hy=hydrophobic amino acid) is set forth that, after insertion in the light chain, is to enhance its persistency. Finally this patent application suggests a modified botulinum toxin type A, in which the light chain is mutated (alanine to leucine at the positions 427 and 428).

In view of the above described prior art it was an object of the inventors to provide an additional or precisely described form of stabilization for any type of botulinum toxin preferably, however, for type A, B, and C1. Along with this the object of the inventors was to provide stable variants/analogs of the natural botulinum toxins which in comparison to the respective unmodified botulinum toxins have an increased in vivo stability. This means, firstly, that the biological activity (according to the invention biological activity is defined as total activity comprising the enzymatic/catalytic activity of the light chain as well as the required neurotoxin binding to the target cell and the translocation of the light chain into the target cell) of the botulinum toxin variant/analog shall be at most marginally (according to the above definition), and preferably not at all, decreased and, secondly, that, in spite of its modification, the light chain is translocated to its site of action, the cytosol of the motoneuron.

In contrast to the already aforementioned US 20020197278 the objective forming the basis of the present application does not aim to block antigenic determinants, to decrease the antigenicity of the toxins or to restrict their diffusion away from the injection site.

The inventors of the present application surprisingly found, that the light chain of botulinum toxins can be specifically PEGylated at its N-terminus via insertion of at least one cysteine residue without simultaneously impairing or even inhibiting the biological activity (according to the definition given above) of the botulinum toxins. Such a PEGylated botulinum toxin is characterized by a surprisingly higher in vivo stability (significant increase of HL and therewith an extended (pharmacological) duration of action).

The (therapeutic) duration of action of the natural botulinum toxins in the patient depends on the serotype. Botulinum toxin type A is characterized by the longest duration of action of about 3 month. The duration of action of botulinum toxin type C is of similar length as that of type A, whereas botulinum toxin type B has a shorter duration of action. The effect of botulinum toxins type E and F lasts only about 2 weeks in each case. The short duration of action of these two types does not allow their clinical application for the treatment of dystonia. The present invention allows (1) the clinical application of all botulinum toxins, even those having so far short-term activity, and (2) a more advantageous therapy with the already therapeutically utilized type A and B toxins, as these need not be administered every three month, but e.g., only every six month.

DESCRIPTION OF THE FIGURES AND SEQUENCES

FIG. 1: Summary of the oligonucleotides (SEQ ID NO:1 to 14) which have been employed in the cloning of the recombinant toxins and toxin fragments. Recognition sequences for restriction endonucleases are underlined. The long sequences with the SEQ ID NOs: 16 and 15 show examples for a recombinant (mutated) botulinum neurotoxin type A with attached cysteine residue N-terminal to a histidine tag (consisting of 10 histidine residues) or a DNA that encodes it. The proline residue at the N-terminus of the native toxins (position 1) that is monocystronically expressed and translated was replaced by an alanine residue to create a cleavage site in the multicloning site (MCS) of the vector. The vector comprises the coding sequence for the His-tag precisely in the 5'-vicinity of this MCS. In addition a sequence which is recognized by $E.$ $coli$ cells has already been inserted in place of the native loop between the light and the heavy chain whereupon the native pre-peptide (N-light chain-loop-heavy chain-C) is already cleaved into the active two-chain neurotoxin without the addition of exogenous proteases and obtained as such during the recombinant production of the neurotoxin.

FIG. 2: Analysis of the PEGylation and control batches of C—H$_{10}$-BoNT/A (Example 5) in SDS polyacrylamide gels under non-reducing conditions. Lane 1: molecular weight marker; Lane 2: control batch; Lane 3: PEGylation batch.

DESCRIPTION OF THE INVENTION

In order to solve the stated object (see above) the inventors have developed modified botulinum toxins. One aspect of the invention therefore relates to a modified botulinum toxin comprising a natural heavy chain and a modified light chain, wherein the modification of the light chain is that it comprises (1) an extension of the chain on its N-terminus which has the following structure in the direction from the N- to the C-terminal end: —(C)$_n$-(tag)$_m$-(X)$_l$—, wherein C represents a cysteine residue, tag represents any tag, e.g. a Strep-tag or a His-tag, and X represents the residue of any naturally occurring amino acid, n represents an integer from 1 to 50, m represents 0 or 1, and l represents 0 or an integer from 1 to 50, and (2) that at least one of the cysteine residues in the extension of the chain is coupled to at least one chain of PEG. Such a modified botulinum toxin is hereinafter also referred to as PEGylated mutated botulinum or neurotoxin.

According to a preferred embodiment, the following conditions apply:

n=1, 2 or 3, m=0 or l=0 or l≠0,
n=1, m=1, l=0; n=2, m=1, l=0; n=3, m=1, l=0;
n=1, m=0, l=0; n=2, m=0, l=0; n=3, m=0, l=0;
n=1, m=1, l≠0; n=2, m=1, l≠0; n=3, m=1, l≠0;
n=1, m=0, l≠0; n=2, m=0, l≠0; n=3, m=0, l≠0;

wherein the toxins per molecule are coupled to one, to two or to three PEG molecules, depending on whether n=1, 2 or 3.

Thus preferably those modified botulinum toxins (especially of the types A, B, and C1) fall within the aforementioned modified botulinum toxins of the present invention whose light chain is modified in such a way that it comprises an extension of the chain, wherein the extended chain has one of the following sequences:

—$(C)_1$-$(tag)_1$-$(X)_0$—, —$(C)_2$-$(tag)_1$-$(X)_0$—, —$(C)_3$-$(tag)_1$-$(X)_0$—, —$(C)_4$-$(tag)_1$-$(X)_0$—, —$(C)_5$-$(tag)_1$-$(X)_0$—,
—$(C)_1$-$(tag)_1$-$(X)_1$—, —$(C)_2$-$(tag)_1$-$(X)_1$—, —$(C)_3$-$(tag)_1$-$(X)_1$—, —$(C)_4$-$(tag)_1$-$(X)_1$—, —$(C)_5$-$(tag)_1$-$(X)_1$—,
—$(C)_1$-$(tag)_1$-$(X)_2$—, —$(C)_2$-$(tag)_1$-$(X)_2$—, —$(C)_3$-$(tag)_1$-$(X)_2$—, —$(C)_4$-$(tag)_1$-$(X)_2$—, —$(C)_5$-$(tag)_1$-$(X)_2$—,
—$(C)_1$-$(tag)_1$-$(X)_3$—, —$(C)_2$-$(tag)_1$-$(X)_3$—, —$(C)_3$-$(tag)_1$-$(X)_3$—, —$(C)_4$-$(tag)_1$-$(X)_3$—, —$(C)_5$-$(tag)_1$-$(X)_3$—,
—$(C)_1$-$(tag)_1$-$(X)_4$—, —$(C)_2$-$(tag)_1$-$(X)_4$—, —$(C)_3$-$(tag)_1$-$(X)_4$—, —$(C)_4$-$(tag)_1$-$(X)_4$—, —$(C)_5$-$(tag)_1$-$(X)_4$—, etc.

wherein in any of the above listed 25 preferred embodiments m can also be 0 instead of 1, and/or in each case all cysteine residues occurring in the extension of the light chain are also PEGylated.

Of course l can also be any integer from 11 to 50 or above 50, most preferred above 100 or above 250. However, the greater l is, the longer the light chain becomes without the enzymatic/catalytic activity or the (total) biological activity (according to the above definition) being compromised by a specific upper limit for the length of the light chain. For reasons of practicability, however, an upper limit to l of 10-20 is preferred so that preferred values for l are in the range of 1-10, unless l is 0, which is especially preferred.

Appropriate considerations also apply to n, wherein according to the invention its upper limit has been set to 50 for practical and economical reasons. Preferably n is in the range of 1-10, more preferred 1-5, so as not to insert, or not to have to insert, too many PEG molecules (as all inserted cysteine residues are preferably PEGylated), and not to deprive the resulting PEGylated mutated botulinum/neurotoxin of its biological activity according to the aforementioned definition. This can easily occur, if too many cysteine and PEG residues are inserted or inserted at incorrect positions, as the light chain, perhaps despite the binding of the toxin to the target cell, is not translocated into the target cell.

The structure of botulinum toxin type A was published by Lacy & Stevens 1998 (Nat. Struct. Biol. 5, 898-902), the structure of botulinum toxin type B by Swaninathan & Eswaramoorthy (Nat. Struct. Biol 7, 693-699 (2000)). Therefore the structure of the light chains is also known and one can determine which region of the heavy and the light chain, respectively are at the protein surface and thus may be suitable for a coupling with PEG. The frequently chosen procedure of binding an appropriately activated PEG (e.g., PEG-succinimidyl-propionate) to the ε-amino group of lysine residues did not seem promising to the inventors. An activated PEG can react with numerous lysine residues—even in the binding region of the heavy chain—and this leads experimentally to a drastic inactivation.

Instead, the inventors identified amino acid residues of the light chain which are suited initially to be replaced by at least one cysteine residue and subsequently to be PEGylated on the at least one inserted cysteine residue. These modified botulinum toxins, hereinafter to be characterized in more detail, which are also a preferred embodiment of the present invention and have as conjugates with PEG a sufficient biological (including enzymatic/catalytic) activity (which by definition corresponds at least to 20%, preferably to 30-40%, to 50-70% or even to 75-95% of the biological activity of the unmodified protein) with simultaneously increased stability (in comparison to the corresponding native neurotoxins) and will hereinafter also be referred to as PEGylated mutated botulinum or neurotoxins of the present invention.

These latter modified botulinum toxins of the present invention are also conjugates of mutated botulinum toxins with PEG. These modified botulinum toxins are also coupled to PEG via separately inserted cysteine residues. For this purpose at least one, but optionally also 2, 3, 4, 5, 10 or even all 20 of the first 20 amino acid residues of the N terminal end of the light chain of the respective botulinum toxin is in each case replaced by a cysteine residue. These modified botulinum toxins also comprise a natural heavy chain and a modified light chain, wherein the modification of the light chain is such that at least one up to maximally 20 of the amino acid residues occurring naturally at the N terminus are mutated to a cysteine residue. If applicable they comprise an additional N terminal extension, such that the sequence of the light chain has the following structure in the direction from the N-terminus to the C-terminus:

-$(tag)_m$-$(X)_l$-BoNT(X1-20C), wherein

C represents a cysteine residue,
tag represents any tag, e.g. a Strep-tag or a His-tag, and
X represents the residue of any naturally occurring amino acid,
m represents 0 or 1, and
l represents 0 or an integer from 1 to 50.

At least one of the maximally 20 cysteine residues at the N-terminus is coupled to at least one chain of PEG.

Hence there result mutants for BoNT/A, which are characterized by at least one—and not more than twenty—of the following replacements of amino acid residues, such that a PEGylation can occur at the inserted cysteine residues. P1C, F2C, V3C, N4C, K5C, Q6C, F7C, N8C, Y9C, K10C, D11C, P12O, V13C, N14C, G15C, V16O, D17C, I18C, A19C, Y20C According to a preferred embodiment, the following conditions apply:

m=1, l=0, only one out of the 20 N-terminal amino acid residues is replaced by a cysteine residue, more preferable only the residue at position 1, 2, 3, 4, 5, 6, 7, 8, 9, or 10;

m=0, l=0, only one out of the 20 N-terminal amino acid residues is replaced by a cysteine residue, more preferable only the residue at position 1, 2, 3, 4, 5, 6, 7, 8, 9, or 10;

m=1, l≠0, only one out of the 20 N-terminal amino acid residues is replaced by a cysteine residue, more preferable only the residue at position 1, 2, 3, 4, 5, 6, 7, 8, 9, or 10;

m=0, l≠0, only one out of the 20 N-terminal amino acid residues is replaced by a cysteine residue, more preferable only the residue at position 1, 2, 3, 4, 5, 6, 7, 8, 9, or 10;

m=1, l≠0, only two out of the 20 N-terminal amino acid residues are replaced by a cysteine residue, more preferable only the residues at the positions 1 and 3, 1 and 4, 2 and 4, 1 and 5, 2 and 5, 3 and 5, 1 and 6, 2 and 6, 3 and 6, or 4 and 6;

m=0, l≠0, only two out of the 20 N-terminal amino acid residues are replaced by a cysteine residue, more preferable only the residues at the positions 1 and 3, 1 and 4, 2 and 4, 1 and 5, 2 and 5, 3 and 5, 1 and 6, 2 and 6, 3 and 6, or 4 and 6;

m=1, l≠0, only two out of the 20 N-terminal amino acid residues are replaced by a cysteine residue, more preferable only the residues at the positions 1 and 3, 1 and 4, 2 and 4, 1 and 5, 2 and 5, 3 and 5, 1 and 6, 2 and 6, 3 and 6, or 4 and 6;

m=0, l≠0, only two out of the 20 N-terminal amino acid residues are replaced by a cysteine residue, more preferable only the residues at the positions 1 and 3, 1 and 4, 2 and 4, 1 and 5, 2 and 5, 3 and 5, 1 and 6, 2 and 6, 3 and 6, or 4 and 6;

m=1, l=0, only two out of the 20 N-terminal amino acid residues are replaced by a cysteine residue, more preferable only the residues at the positions 1 and 2, 2 and 3, 3 and 4, 4 and 5, or 5 and 6;

m=0, l=0, only two out of the 20 N-terminal amino acid residues are replaced by a cysteine residue, more preferable only the residues at the positions 1 and 2, 2 and 3, 3 and 4, 4 and 5, or 5 and 6;

m=1, l≠0, only two out of the 20 N-terminal amino acid residues are replaced by a cysteine residue, more preferable only the residues at the positions 1 and 2, 2 and 3, 3 and 4, 4 and 5, or 5 and 6;

m=0, l≠0, only two out of the 20 N-terminal amino acid residues are replaced by a cysteine residue, more preferable only the residues at the positions 1 and 2, 2 and 3, 3 and 4, 4 and 5, or 5 and 6, wherein the toxins per molecule are coupled to one or two PEG molecules, depending on whether only one or two amino acid residues have been replaced by (one) cysteine residue(s) at the N-terminus.

Therefore preferably those botulinum toxins (especially of the types A, B, and C1) fall within the aforementioned modified botulinum toxins whose light chain is modified in such a way that it comprises an extension of the chain at its N-terminus, terminus, wherein the N-terminus of the extended chain has one of the following sequences:

-(tag)$_1$-(X)$_0$-BoNT(P1C), -(tag)$_1$-(X)$_0$-BoNT(F2C), -(tag)$_1$-(X)$_0$-BoNT(V3C), -(tag)$_1$-(X)$_0$-BoNT(N4C), -(tag)$_1$-(X)$_0$-BoNT(K5C), -(tag)$_1$-(X)$_1$-BoNT(P1C), -(tag)$_1$-(X)$_1$-BoNT(F2C), -(tag)$_1$-(X)$_1$-BoNT(V3C), -(tag)$_1$-(X)$_1$-BoNT(N4C), -(tag)$_1$-(X)$_1$-BoNT(K5C), -(tag)$_1$-(X)$_2$-BoNT(P1C), -(tag)$_1$-(X)$_2$-BoNT(F2C), -(tag)$_1$-(X)$_2$-BoNT(V3C), -(tag)$_1$-(X)$_2$-BoNT(N4C), -(tag)$_1$-(X)$_2$-BoNT(K5C), -(tag)$_1$-(X)$_3$-BoNT(P1C), -(tag)$_1$-(X)$_3$-BoNT(F2C), -(tag)$_1$-(X)$_3$-BoNT(V3C), -(tag)$_1$-(X)$_3$-BoNT(N4C), -(tag)$_1$-(X)$_3$-BoNT(K5C), -(tag)$_1$-(X)$_4$-BoNT(P1C), -(tag)$_1$-(X)$_4$-BoNT(F2C), -(tag)$_1$-(X)$_4$-BoNT(V3C), -(tag)$_1$-(X)$_4$-BoNT(N4C), -(tag)$_1$-(X)$_4$-BoNT(K5C), etc.

wherein in any of the above listed 25 preferred embodiments m can also be 0 instead of 1, and/or in each case all N-terminally inserted cysteine residues are also PEGylated.

Of course, l can also be any integer from 11 to 50 or above 50, most preferred above 100 or above 250. However, the greater l, the longer the light chain without the enzymatic/catalytic activity or the (total) biological activity of the neurotoxin becoming compromised with regard to the above mentioned definition by a specific upper limit for the length of the light chain. For reasons of practicability, however, an upper limit of l of 10-20 is preferred, so that preferred values for l are in the range of 1-10, unless l is 0, which is especially preferred.

Unless explicitly specified otherwise, the following explanations apply to the modified botulinum toxins of the present invention, regardless whether it is the variant with inserted cysteine residue(s) in the N-terminal extension of the light chain or the variant with inserted cysteine residue(s) at the N-terminal end of the light chain.

Preferably, the modified botulinum toxin is a modified botulinum toxin derived from BoNT/A, BoNT/B, or BoNT/C1, but it also can be a botulinum toxin of the types D, E, F, or G. It is also preferred that on the one hand all artificially inserted cysteine residues (preferably 1-10 cysteine residues are inserted) comprise at least one PEG chain, but on the other hand none of the naturally occurring cysteine residues of the heavy and light chains of the botulinum toxin is PEGylated.

It is self-explanatory to a person skilled in the art, that the relevance of the tag (m=1) resides in the easier purification of the recombinantly (e.g., in E. coli) produced modified botulinum toxin of the present invention. Thus, the tag is not used to increase the stability of the neurotoxin or its biological activity, but allows the simplified and almost quantitative isolation of the modified botulinum toxin from the bacterial culture.

Regarding the question of an appropriate choice of n (in case of the variant with inserted cysteine residue(s) in the N-terminal extension of the light chain) or the number and position of the amino acid residues to be replaced by cysteine residues (in case of the variant with inserted cysteine residue(s) at the N-terminal end of the light chain) one has to consider that preferably only as many cysteine residues are inserted as PEGylations are to be carried out (the same applies to the case, where l≠0 and at least one amino acid residue X is a cysteine residue). All of these inserted cysteine residues can preferably be PEGylated, and completely at that, without, and that is the surprising finding of the inventors, even one of the cysteine residues occurring naturally in botulinum toxin being PEGylated on the heavy or on the light chain (besides one intra- and intermolecular disulfide bridge each, botulinum toxin type A e.g. exhibits three additional cysteine residues in the heavy chain ($C_{791}$, $C_{967}$, $C_{1060}$) as well as two additional cysteine residues in the light chain ($C_{134}$ and $C_{165}$)). In this manner, a consistent (homogeneous) product in the form of a PEGylated mutated botulinum toxin can be obtained. Furthermore, it is reasonable to avoid too many cysteine or PEG residues being inserted or inserted at incorrect positions for an additional reason. This is so because (i) the toxin possibly may then become too bulky to bind to the target cell and/or (ii) the light chain is, perhaps despite binding of the toxin to the target cell, not sufficiently translocated into the target cell. In other words, the insertion of only one cysteine residue in this or that variant and its PEGylation routinely accomplishes the purpose of the invention and is therefore especially preferred.

Accordingly, the PEGylated mutated botulinum/neurotoxins in accordance with the present invention are, like the corresponding natural (native) botulinum/neurotoxins, biologically and enzymatically (i.e., catalytically) active or exhibit in the sense of the definition given above not more than a marginally decreased biological and enzymatic/catalytic activity, but are more stable, partly even substantially more stable, than their natural precursor toxins from which they were derived. Furthermore, a PEGylated mutated botulinum toxin is preferred, whose PEGylated mutated (modified) light chain exhibits a higher stability in the cytosol of the motoneuron than the unmodified light chain of the corresponding native botulinum toxin.

As described above, the PEGylation of the light chain results in an increased stability compared to the unmodified light chain. In accordance with the invention the PEG chain is attached to the light chain thus, that, firstly, its enzymatic activity is unchanged or at most marginally decreased (according to the definition given above), and, secondly, the modified light chain like the unmodified chain is translocated into the cytosol of the motoneuron.

The His-tag as well as other tags, e.g., the Strep-tag, allows the straightforward isolation of the mutated neurotoxin from the lysate of transformed bacteria (e.g., E. coli). At the DNA level it is most simply attached in 5'-direction to the coding region of the neurotoxin gene. In the case of the His-tag the isolation occurs by use of affinity chromatography on Ni-NTA-sepharose. In the next step, the mutated neurotoxin that is isolated in this way is coupled to activated PEG. A series of activated PEG derivatives, e.g., PEG-maleimide, PEG-vinylsulfone, PEG-iodoacetamide, and PEG-orthopyridyl-disulfide are provided by Nektar Therapeutics, and instructions for the PEGylation are supplied. In accordance with the invention these PEG derivatives may comprise different chain lengths: e.g., PEG derivatives with molecular weights of 5,000 Dalton, 10,000 Dalton, 20,000 Dalton, and 30,000 Dalton are commercially available and to be used in accordance with the invention.

For the determination of the protease activity of the mutated and subsequently PEGylated botulinum toxin the cleavage of the SNARE protein corresponding to the serotype is quantitatively recorded. The activity is then compared to the activity of (i) the native neurotoxin (of the corresponding serotype), (ii) the mutated neurotoxin with tag for the simplified isolation and/or (iii) the mutated neurotoxin without tag. The activity of the mutated neurotoxin and of the PEGylated mutated neurotoxin in accordance with the present invention is similar to the activity of the native (non-mutated) neurotoxin (that is, the biological activity, according to the definition above, of the mutated neurotoxin and of the modified neurotoxin according to the invention is at most marginally decreased in the sense of the definition given above compared to the biological activity of the neurotoxin).

The total activity of the PEGylated neurotoxin is initially determined in an ex-vivo model, the so-called diaphragm or hemidiaphragm-assay. Here the paralyzing activity is determined on a nerve-muscle preparation. In accordance with the invention the biological activity of the modified as well as of the mutated and subsequently PEGylated neurotoxin is at least 20%, preferably 30-40% or 50-70% or even 75-95% of the biological activity of the unmodified (native) protein (biological activity is also to be understood according to the definition given above).

The toxicity of the PEGylated mutated neurotoxin according to the invention can be tested in the mouse $LD_{50}$-assay, whereby the dose is being determined that after i.p. application is lethal for half the mice from a group.

The duration of action of the PEGylated mutated neurotoxin according to the invention is determined in vivo, also with a mouse. The period during which the muscle remains paralyzed is determined after injection of a sublethal dose of a PEGylated mutated botulinum toxin type A according to the present invention or of the corresponding native botulinum toxin in the gastrocnemius muscle of the hindpaw. The paralysis potency is classified by way of a chart. The duration of action, which is shorter in the mouse than in men, is extended by 30-150% depending on the modified botulinum toxin type A used (measured in comparison to the non-PEGylated and unmutated botulinum toxin type A).

The PEGylated mutated botulinum toxin according to the present invention can be processed in an appropriate formulation to a finished drug product, which includes a dose (or an integral multiple of the dose) in the range of the therapeutic dose (e.g., 100 $LD_{50}$-units per injection vial). According to a preferred embodiment the pharmaceutical composition is stabilized without addition of human serum albumin (HSA). However, it may also be stabilized with human serum albumin (HSA). In this regard the use of a HSA-free composition for the stabilization of PEGylated active protein substances as described in WO 2005/007185 is especially preferred. In accordance with a further preferred embodiment the pharmaceutical composition of the present invention is in lyophilized form or fluid. Both forms are suitable, optionally after uptake in an appropriate solvent, for i.m. injection in the muscle to be treated.

The PEGylated mutated botulinum toxin with greater stability and half life or the pharmaceutical exhibiting these can be used for therapy of various dystonia as spasmodic dystonia, laryngeal dystonia, cervical dystonia, focal hand dystonia, blepharospasm, strabism, cerebral paresis, hemifacial spasms, spasticity, spasmodic colitis, anismus, TICS, tremors, bruxism, anal fissure, achalasia, dysphagia, hyperhidrosis as well as for removal of facial wrinkles.

Additional aspects of the present investigation relate to (1) a nucleic acid, which encodes the above explicitly described modified botulinum toxin with increased stability (especially the nucleic acid is DNA); (2) a vector, comprising the nucleic acid according to (1); and (3) a host cell, comprising the vector according to (2) (especially the host cell is a prokaryotic, in particular, an E. coli host cell).

The following examples illustrate the invention in detail without limiting the invention to the aforementioned specific parameters.

EXAMPLES

Example 1

Cloning and Expression of Botulinum Neurotoxin Type A (BoNT/A)

For cloning the DNA sequences of the light chain as well as of the translocation domain, chromosomal DNA was isolated from a culture of *Clostridium botulinum* type A (strain ATCC 3502). A coding gene fragment with modified loop sequence for the light chain of BoNT/A was obtained by using PCR amplification with the primers SEQ ID NO:1 and SEQ ID NO:2. The PCR amplificate was cloned via the restriction cleavage sites for Nco I and Bgl II into the expression plasmid pQE-$H_{10}$, which was derived from pQE-60 and encodes a His-tag (consisting of 10 histidine residues) at the 5'-end of the cloning site. The plasmid pQE-$H_{10}$-BoNT/A-L was generated by this cloning method. A coding gene fragment for the heavy chain of BoNT/A was obtained by using PCR amplification with the primers SEQ ID NO:3 and SEQ ID NO:4. It was cloned by means of the restriction cleavage sites for Stu I and Bgl II to the 3'-end of the loop sequence of the light chain in pQE-$H_{10}$-BoNT/A-L (plasmid pQE-$H_{10}$-BoNT/A). The *E. coli* expression strain M15[pREP4] (Qiagen) was transformed with the plasmid pQE-$H_{10}$-BoNT/A. The expression of the recombinant toxins was realized by a graded induction with 500 µM IPTG (final concentration) at 25° C. over night. The cells were solubilized through lysozyme and ultrasound treatment in a 50 mM phosphate buffer at pH 8.0 with 300 mM NaCl. The centrifuged lysate was incubated for 5 h at room temperature and after intermittent storage at −20° C. chromatographed on a Ni-NTA agarose column. Finally the elution fractions were dialyzed against a coupling buffer (100 mM sodium dihydrogen phosphate pH 7.5, 150 mM NaCl, 10 mM EDTA) and the protein concentration was determined. An analysis on SDS polyacrylamide gel showed that under reducing conditions two strong bands at about 50 kDa and 100 kDa as well as a weak band at 150 kDa were stained with Coomassie whereas under non-reducing conditions only one band was observed at about 150 kDa, which corresponds to the banding pattern of a botulinum neurotoxin type A in its prevailing two-chain, disulfide-bridged structure.

Example 2

Cloning and Expression of Botulinum Neurotoxin Type B (BoNT/B)

Cloning and expression of a botulinum neurotoxin type B equipped with a histidine tag (consisting of 10 histidine residues) at the N-terminus was carried out analogously to the type A toxin. Chromosomal DNA from *Clostridium botulinum* type B (strain Okra) as well as the primer SEQ ID NO:5 and SEQ ID NO:6 or SEQ ID NO:7 and SEQ ID NO:8 were employed for the amplification of the light and heavy chains.

Example 3

Cloning and Expression of Botulinum Neurotoxin Type C1 (BoNT/C1)

Cloning and expression of a botulinum neurotoxin type C1 equipped with a histidine tag (consisting of 10 histidine residues) at the N-terminus was done analogously to the type A toxin. Chromosomal DNA from *Clostridium botulinum* type C (strain 205) as well as the primer SEQ ID NO:9 and SEQ ID NO:10 or SEQ ID NO:11 and SEQ ID NO:12 were employed for the amplification of the light and heavy chain.

Example 4

Cloning and Expression of C—$H_{10}$-BoNT/A

To allow for a N-terminal PEGylation a cysteine residue was attached to the amino acid sequence N-terminal to the histidine tag (consisting of 10 histidine residues). This was achieved through site-directed mutagenesis in the sequence region of pQE-$H_{10}$-BoNT/A, which encodes the His-tag. The QuickChange Site Directed Mutagenesis Kit of Stratagene was employed. The mutagenesis reaction was carried out with the primers SEQ ID NO:13 and SEQ ID NO:14. The nucleotide exchange in the DNA sequence was verified by DNA sequencing of the isolated clones. The expression and the purification of the mutated toxin were carried out analogously to Example 1.

Example 5

PEGylation of C—$H_{10}$-BoNT/A 1.2 mg of C—$H_{10}$-BoNT/A was incubated for 30 minutes in 1 mM DTT to reduce the disulfide-bridged dimers. For separation of the reducing agent a buffer exchange to coupling buffer was carried out on a PD-10 column. The toxin solution was concentrated to 3.6 mg/ml by means of ultrafiltration. A small aliquot was incubated untreated as control sample, the remainder of the solution was mixed with a 5-fold molar excess of mPEG-Mal-5000 (Nektar Therapeutics) and rotated at ambient temperature over night. In order to avoid derivatization reactions on further cysteine residues during the sample preparation for SDS-PAGE, the PEGylation reagent was saturated with a 5-fold excess of L-cysteine. The SDS gel showed a strong additional band with slightly reduced mobility in comparison to the control batch under non-reducing conditions, while the intensity of the original toxin band at 150 kDa was significantly decreased (FIG. 2).

Example 6

In Vitro-Activity Assay

Determination of the specific protease activity (that is, the catalytic activity without binding or translocation) of the PEGylated mutated BoNT/A derivative was done in the ELISA format. For this purpose, a recombinant polypeptide was cloned, consisting in the N-terminal region of the common fusion partner glutathion-S-transferase (GST) and of a C-terminal peptide sequence, which comprises the C-terminal 17 amino acid residues of SNAP 25. These 17 amino acid residues represent the region of the substrate protein SNAP 25, in which BoNT/A specifically cleaves. After coating of a microtiter plate with the fusion protein incubation was done with $H_{10}$-BoNT/A as reference sample or with the mutants in their PEGylated and non-PEGylated form. The detection of the cleavage products generated in each case was done with an antibody, which specifically detects the newly formed C-terminus. The values for C—$H_{10}$-BoNT/A in its non-PEGylated as well as PEGylated form and for BoNT/A (reference sample) are listed in Table 3. Considering the variation limit of the assay one can observe that through the introduction of the mutation and the subsequent PEGylation the catalytic activity of the botulinum toxin was not decreased, but instead was enhanced.

TABLE 3

| | Relative activity [%] |
|---|---|
| $H_{10}$-BoNT/A | 100 |
| C—$H_{10}$-BoNT/A | 100 |
| mPEG-C—$H_{10}$-BoNT/A | 121.1 |

The specific activity was determined in protease units/ng protein.

Example 7

Determination of the Ex-Vivo Activity in the Hemidiaphragm Assay

For the determination of the total activity of the toxin derivatives, i.e., the binding of the modified neurotoxin to the receptor of the target cells and the translocation into the nerve cell and proteolysis of the SNARE substrate, the paralysis time of a nerve-muscle preparation from mouse was determined after intoxication. Again $H_{10}$-BoNT/A served as a reference sample. The values of the relative activity are listed in Table 4. The reduction in the activity of the modified botulinum toxins according to the present invention to 20-30% as compared to the reference sample is obviously based on the reduced ability of the toxin to bind to the target cells and on the reduced ability to translocate the toxin into the target cells.

TABLE 4

| | Relative activity [%] |
|---|---|
| $H_{10}$-BoNT/A | 100 |
| C—$H_{10}$-BoNT/A | 22.5 |
| mPEG-C—$H_{10}$-BoNT/A | 30 |

Example 8

Duration of Action of PEGylated Botulinum Toxin Type A

The duration of action of PEGylated mutated botulinum toxin (mPEG-C—$H_{10}$-BoNT/A) was assayed with CD 1-mice. 10 mice each received i.m. injections (2×0.05 mL) of (i) mutated, (ii) PEGylated mutated or (iii) native botulinum toxin in a dosage of 0.4 or 0.6 $LD_{50}$-units/mouse (in physiological saline+1 mg/mL HSA) into the gastrocnemius muscle of the hindpaw. Afterwards the paralysis of the muscle was evaluated on a daily basis by using a chart (minimal, gentle, severe paralysis). No more paralysis of the muscle was observed after 25 days in the animals treated with the native neurotoxin. In the animals treated with the mutated or PEGylated mutated botulinum toxin, the duration of action was extended for 7-20 days.

```
                         SEQUENCE LISTING

<160> NUMBER OF SEQ ID NOS: 16

<210> SEQ ID NO 1
<211> LENGTH: 35
<212> TYPE: DNA
<213> ORGANISM: Artificial sequence
<220> FEATURE:
<223> OTHER INFORMATION: Synthetic Primer

<400> SEQUENCE: 1
accactccat ggcatttgtt aataaacaat ttaat                        35

<210> SEQ ID NO 2
<211> LENGTH: 67
<212> TYPE: DNA
<213> ORGANISM: Artificial sequence
<220> FEATURE:
<223> OTHER INFORMATION: Synthetic Primer

<400> SEQUENCE: 2
accaccagat ctatttaagg ccttggatcc acgcggaact aatgatttag ttttagaagt   60
tattatc                                                            67

<210> SEQ ID NO 3
<211> LENGTH: 37
<212> TYPE: DNA
<213> ORGANISM: Artificial sequence
<220> FEATURE:
<223> OTHER INFORMATION: Synthetic Primer

<400> SEQUENCE: 3
accaccaggc cttaaatgat ttatgtatca aagttaa                      37

<210> SEQ ID NO 4
<211> LENGTH: 39
<212> TYPE: DNA
<213> ORGANISM: Artificial sequence
<220> FEATURE:
<223> OTHER INFORMATION: Synthetic Primer

<400> SEQUENCE: 4
accaccagat ctttacagtg gcctttctcc ccatccatc                    39

<210> SEQ ID NO 5
<211> LENGTH: 39
<212> TYPE: DNA
<213> ORGANISM: Artificial sequence
<220> FEATURE:
<223> OTHER INFORMATION: Synthetic Primer

<400> SEQUENCE: 5
accactccat ggcagttaca ataaataatt ttaattata                    39

<210> SEQ ID NO 6
<211> LENGTH: 85
```

```
<212> TYPE: DNA
<213> ORGANISM: Artificial sequence
<220> FEATURE:
<223> OTHER INFORMATION: Synthetic Primer

<400> SEQUENCE: 6
accactaggc cttggatcca cgtggaacca atgatttagt tttagaagtt attatcccac    60
ttttacacat ttgtatctta tatac                                         85

<210> SEQ ID NO 7
<211> LENGTH: 34
<212> TYPE: DNA
<213> ORGANISM: Artificial sequence
<220> FEATURE:
<223> OTHER INFORMATION: Synthetic Primer

<400> SEQUENCE: 7
accactaggc ctcaggaata tgtattgatg ttga                                34

<210> SEQ ID NO 8
<211> LENGTH: 33
<212> TYPE: DNA
<213> ORGANISM: Artificial sequence
<220> FEATURE:
<223> OTHER INFORMATION: Synthetic Primer

<400> SEQUENCE: 8
accaccagat ctttattcag tccacccttc atc                                 33

<210> SEQ ID NO 9
<211> LENGTH: 40
<212> TYPE: DNA
<213> ORGANISM: Artificial sequence
<220> FEATURE:
<223> OTHER INFORMATION: Synthetic Primer

<400> SEQUENCE: 9
accactccat ggcaataaca attaacaact ttaattattc                          40

<210> SEQ ID NO 10
<211> LENGTH: 76
<212> TYPE: DNA
<213> ORGANISM: Artificial sequence
<220> FEATURE:
<223> OTHER INFORMATION: Synthetic Primer

<400> SEQUENCE: 10
gagaataggc cttggatcca cgcggaacta atgatttagt tttagaagtt attatccctc    60
tatgacaaaa ttttgt                                                   76

<210> SEQ ID NO 11
<211> LENGTH: 33
<212> TYPE: DNA
<213> ORGANISM: Artificial sequence
<220> FEATURE:
<223> OTHER INFORMATION: Synthetic Primer

<400> SEQUENCE: 11
accactaggc cttagattgt agagagcttt tag                                 33

<210> SEQ ID NO 12
<211> LENGTH: 44
<212> TYPE: DNA
<213> ORGANISM: Artificial sequence
<220> FEATURE:
```

<223> OTHER INFORMATION: Synthetic Primer

<400> SEQUENCE: 12
accaccagat ctttaagaaa taaatttcca aaaagatgaa gttg         44

<210> SEQ ID NO 13
<211> LENGTH: 42
<212> TYPE: DNA
<213> ORGANISM: Artificial sequence
<220> FEATURE:
<223> OTHER INFORMATION: Synthetic Primer

<400> SEQUENCE: 13
gaggagaaat taactatggg atgtggatcg catcaccatc ac           42

<210> SEQ ID NO 14
<211> LENGTH: 42
<212> TYPE: DNA
<213> ORGANISM: Artificial sequence
<220> FEATURE:
<223> OTHER INFORMATION: Synthetic Primer

<400> SEQUENCE: 14
gtgatggtga tgcgatccac atcccatagt taatttctcc tc           42

<210> SEQ ID NO 15
<211> LENGTH: 3939
<212> TYPE: DNA
<213> ORGANISM: Artificial sequence
<220> FEATURE:
<223> OTHER INFORMATION: mutiertes Botulinum-Neurotoxin Typ A

<400> SEQUENCE: 15

| | | |
|---|---|---|
| atgggatgtg atcgcatca ccatcaccac catcatcacc atcactccat ggcatttgtt | 60 |
| aataaacaat ttaattataa agatcctgta atggtgttg atattgctta tataaaaatt | 120 |
| ccaaatgcag acaaatgca accagtaaaa gcttttaaaa ttcataataa atatgggtt | 180 |
| attccagaaa gagatacatt tacaaatcct gaagaaggag atttaaatcc accaccagaa | 240 |
| gcaaaacaag ttccagtttc atattatgat tcaacatatt taagtacaga taatgaaaaa | 300 |
| gataattatt taagggagt tacaaaatta tttgagagaa tttattcaac tgatcttgga | 360 |
| agaatgttgt taacatcaat agtaagggga ataccatttt ggggtggaag tacaatagat | 420 |
| acagaattaa aagttattga tactaattgt attaatgtga tacaaccaga tggtagttat | 480 |
| agatcagaag aacttaatct agtaataata ggaccctcag ctgatattat acagtttgaa | 540 |
| tgtaaaagct ttggacatga agttttgaat cttacgcgaa atggttatgg ctctactcaa | 600 |
| tacattagat ttagcccaga ttttacattt ggttttgagg agtcacttga agttgataca | 660 |
| aatcctcttt taggtgcagg caaatttgct acagatccag cagtaacatt agcacatgaa | 720 |
| cttatacatg ctggacatag attatatgga atagcaatta atccaaatag gttttttaaa | 780 |
| gtaaatacta atgcctatta tgaaatgagt gggttagaag taagctttga ggaacttaga | 840 |
| acatttgggg gacatgatgc aaagtttata gatagtttac aggaaaacga atttcgtcta | 900 |
| tattattata taagtttaa agatatagca agtacactta taaagctaa atcaatagta | 960 |
| ggtactactg cttcattaca gtatatgaaa aatgttttta aagagaaata tctcctatct | 1020 |
| gaagatacat ctggaaaatt ttcggtagat aaattaaaat ttgataagtt atacaaaatg | 1080 |
| ttaacagaga tttacacaga ggataatttt gttaagtttt taaagtact aacagaaaa | 1140 |
| acatatttga attttgataa agccgtattt aagataaata gtacctaa ggtaaattac | 1200 |

| | |
|---|---|
| acaatatatg atggatttaa tttaagaaat acaaatttag cagcaaactt taatggtcaa | 1260 |
| aatacagaaa ttaataatat gaattttact aaactaaaaa attttactgg attgtttgaa | 1320 |
| ttttataagt tgctatgtgt aagagggata ataacttcta aaactaaatc attagttccg | 1380 |
| cgtggatcca aggccttaaa tgattatgt atcaaagtta ataattggga cttgtttttt | 1440 |
| agtccttcag aagataattt tactaatgat ctaaataaag gagaagaaat tacatctgat | 1500 |
| actaatatag aagcagcaga agaaaatatt agtttagatt taatacaaca atattattta | 1560 |
| acctttaatt ttgataatga acctgaaaat atttcaatag aaaatctttc aagtgacatt | 1620 |
| ataggccaat tagaacttat gcctaatata gaaagatttc ctaatggaaa aaagtatgag | 1680 |
| ttagataaat atactatgtt ccattatctt cgtgctcaag aatttgaaca tggtaaatct | 1740 |
| aggattgctt taacaaattc tgttaacgaa gcattattaa atcctagtcg tgtttataca | 1800 |
| tttttttctt cagactatgt aaagaaagtt aataaagcta cggaggcagc tatgttttta | 1860 |
| ggctgggtag aacaattagt atatgatttt accgatgaaa ctagcgaagt aagtactacg | 1920 |
| gataaaattg cggatataac tataattatt ccatatatag gacctgcttt aaatataggt | 1980 |
| aatatgttat ataagatga ttttgtaggt gctttaatat tttcaggagc tgttattctg | 2040 |
| ttagaattta taccagagat tgcaatacct gtattaggta cttttgcact tgtatcatat | 2100 |
| attgcgaata aggttctaac cgttcaaaca atagataatg ctttaagtaa aagaaatgaa | 2160 |
| aaatgggatg aggtctataa atatatagta acaaattggt tagcaaaggt taatacacag | 2220 |
| attgatctaa taagaaaaaa aatgaaagaa gctttagaaa atcaagcaga agcaacaaag | 2280 |
| gctataataa actatcagta taatcaatat actgaggaag agaaaaataa tattaatttt | 2340 |
| aatattgatg atttaagttc gaaacttaat gagtctataa ataaagctat gattaatata | 2400 |
| aataaatttt tgaatcaatg ctctgtttca tatttaatga attctatgat cccttatggt | 2460 |
| gttaaacggt tagaagattt tgatgctagt cttaaagatg cattattaaa gtatatatat | 2520 |
| gataatagag gaactttaat tggtcaagta gatagattaa aagataaagt taataataca | 2580 |
| cttagtacag atatacccttt tcagctttcc aaatacgtag ataatcaaag attattatct | 2640 |
| acatttactg aatatattaa gaatattatt aatacttcta tattgaattt aagatatgaa | 2700 |
| agtaatcatt taatagactt atctaggtat gcatcaaaaa taaatattgg tagtaaagta | 2760 |
| aattttgatc caatagataa aaatcaaatt caattattta atttagaaag tagtaaaatt | 2820 |
| gaggtaattt taaaaaatgc tattgtatat aatagtatgt atgaaaattt tagtactagc | 2880 |
| ttttggataa gaattcctaa gtattttaac agtataagtc taaataatga atatacaata | 2940 |
| ataaattgta tggaaaataa ttcaggatgg aaagtatcac ttaattatgg tgaaataatc | 3000 |
| tggactttac aggatactca ggaaataaaa caaagagtag ttttttaaata cagtcaaatg | 3060 |
| attaatatat cagattatat aaacagatgg atttttgtaa ctatcactaa taatagatta | 3120 |
| aataactcta aaatttatat aaatggaaga ttaatagatc aaaaaccaat ttcaaattta | 3180 |
| ggtaatattc atgctagtaa taatataatg tttaaattag atggttgtag agatacacat | 3240 |
| agatatattt ggataaaata ttttaatctt tttgataagg aattaaatga aaagaaaatc | 3300 |
| aaagattat atgataatca atcaaattca ggtattttaa aagactttg gggtgattat | 3360 |
| ttacaatatg ataaaccata ctatatgtta aatttatatg atccaaataa atatgtcgat | 3420 |
| gtaaataatg taggtattag aggttatatg tatcttaaag ggcctagagg tagcgtaatg | 3480 |
| actacaaaca tttatttaaa ttcaagtttg tataggggga caaaatttat tataaaaaaa | 3540 |

```
tatgcttctg gaaataaaga taatattgtt agaaataatg atcgtgtata tattaatgta    3600
gtagttaaaa ataaagaata taggttagct actaatgcat cacaggcagg cgtagaaaaa    3660
atactaagtg cattagaaat acctgatgta ggaaatctaa gtcaagtagt agtaatgaag    3720
tcaaaaaatg atcaaggaat aacaaataaa tgcaaaatga atttacaaga taataatggg    3780
aatgatatag ctttatagg atttcatcag tttaataata tagctaaact agtagcaagt    3840
aattggtata atagacaaat agaaagatct agtaggactt tgggttgctc atgggaattt    3900
attcctgtag atgatggatg gggagaaagg ccactgtaa                          3939
```

<210> SEQ ID NO 16
<211> LENGTH: 1312
<212> TYPE: PRT
<213> ORGANISM: Artificial sequence
<220> FEATURE:
<223> OTHER INFORMATION: mutiertes Botulinum-Neurotoxin Typ A

<400> SEQUENCE: 16

```
Met Gly Cys Gly Ser His His His His His His His His Ser
1               5                   10                  15

Met Ala Phe Val Asn Lys Gln Phe Asn Tyr Lys Asp Pro Val Asn Gly
                20                  25                  30

Val Asp Ile Ala Tyr Ile Lys Ile Pro Asn Val Gly Gln Met Gln Pro
            35                  40                  45

Val Lys Ala Phe Lys Ile His Asn Lys Ile Trp Val Ile Pro Glu Arg
        50                  55                  60

Asp Thr Phe Thr Asn Pro Glu Glu Gly Asp Leu Asn Pro Pro Pro Glu
65                  70                  75                  80

Ala Lys Gln Val Pro Val Ser Tyr Tyr Asp Ser Thr Tyr Leu Ser Thr
                85                  90                  95

Asp Asn Glu Lys Asp Asn Tyr Leu Lys Gly Val Thr Lys Leu Phe Glu
            100                 105                 110

Arg Ile Tyr Ser Thr Asp Leu Gly Arg Met Leu Leu Thr Ser Ile Val
        115                 120                 125

Arg Gly Ile Pro Phe Trp Gly Gly Ser Thr Ile Asp Thr Glu Leu Lys
    130                 135                 140

Val Ile Asp Thr Asn Cys Ile Asn Val Ile Gln Pro Asp Gly Ser Tyr
145                 150                 155                 160

Arg Ser Glu Glu Leu Asn Leu Val Ile Gly Pro Ser Ala Asp Ile
                165                 170                 175

Ile Gln Phe Glu Cys Lys Ser Phe Gly His Glu Val Leu Asn Leu Thr
            180                 185                 190

Arg Asn Gly Tyr Gly Ser Thr Gln Tyr Ile Arg Phe Ser Pro Asp Phe
        195                 200                 205

Thr Phe Gly Phe Glu Glu Ser Leu Glu Val Asp Thr Asn Pro Leu Leu
    210                 215                 220

Gly Ala Gly Lys Phe Ala Thr Asp Pro Ala Val Thr Leu Ala His Glu
225                 230                 235                 240

Leu Ile His Ala Gly His Arg Leu Tyr Gly Ile Ala Ile Asn Pro Asn
                245                 250                 255

Arg Val Phe Lys Val Asn Thr Asn Ala Tyr Tyr Glu Met Ser Gly Leu
            260                 265                 270

Glu Val Ser Phe Glu Glu Leu Arg Thr Phe Gly Gly His Asp Ala Lys
        275                 280                 285

Phe Ile Asp Ser Leu Gln Glu Asn Glu Phe Arg Leu Tyr Tyr Tyr Asn
```

-continued

```
            290                 295                 300
Lys Phe Lys Asp Ile Ala Ser Thr Leu Asn Lys Ala Lys Ser Ile Val
305                 310                 315                 320

Gly Thr Thr Ala Ser Leu Gln Tyr Met Lys Asn Val Phe Lys Glu Lys
                325                 330                 335

Tyr Leu Leu Ser Glu Asp Thr Ser Gly Lys Phe Ser Val Asp Lys Leu
                340                 345                 350

Lys Phe Asp Lys Leu Tyr Lys Met Leu Thr Glu Ile Tyr Thr Glu Asp
                355                 360                 365

Asn Phe Val Lys Phe Lys Val Leu Asn Arg Lys Thr Tyr Leu Asn
370                 375                 380

Phe Asp Lys Ala Val Phe Lys Ile Asn Ile Val Pro Lys Val Asn Tyr
385                 390                 395                 400

Thr Ile Tyr Asp Gly Phe Asn Leu Arg Asn Thr Asn Leu Ala Ala Asn
                405                 410                 415

Phe Asn Gly Gln Asn Thr Glu Ile Asn Asn Met Asn Phe Thr Lys Leu
                420                 425                 430

Lys Asn Phe Thr Gly Leu Phe Glu Phe Tyr Lys Leu Leu Cys Val Arg
                435                 440                 445

Gly Ile Ile Thr Ser Lys Thr Lys Ser Leu Val Pro Arg Gly Ser Lys
450                 455                 460

Ala Leu Asn Asp Leu Cys Ile Lys Val Asn Asn Trp Asp Leu Phe Phe
465                 470                 475                 480

Ser Pro Ser Glu Asp Asn Phe Thr Asn Asp Leu Asn Lys Gly Glu Glu
                485                 490                 495

Ile Thr Ser Asp Thr Asn Ile Glu Ala Ala Glu Asn Ile Ser Leu
                500                 505                 510

Asp Leu Ile Gln Gln Tyr Tyr Leu Thr Phe Asn Phe Asp Asn Glu Pro
                515                 520                 525

Glu Asn Ile Ser Ile Glu Asn Leu Ser Ser Asp Ile Ile Gly Gln Leu
                530                 535                 540

Glu Leu Met Pro Asn Ile Glu Arg Phe Pro Asn Gly Lys Lys Tyr Glu
545                 550                 555                 560

Leu Asp Lys Tyr Thr Met Phe His Tyr Leu Arg Ala Gln Glu Phe Glu
                565                 570                 575

His Gly Lys Ser Arg Ile Ala Leu Thr Asn Ser Val Asn Glu Ala Leu
                580                 585                 590

Leu Asn Pro Ser Arg Val Tyr Thr Phe Phe Ser Ser Asp Tyr Val Lys
                595                 600                 605

Lys Val Asn Lys Ala Thr Glu Ala Ala Met Phe Leu Gly Trp Val Glu
610                 615                 620

Gln Leu Val Tyr Asp Phe Thr Asp Glu Thr Ser Glu Val Ser Thr Thr
625                 630                 635                 640

Asp Lys Ile Ala Asp Ile Thr Ile Ile Pro Tyr Ile Gly Pro Ala
                645                 650                 655

Leu Asn Ile Gly Asn Met Leu Tyr Lys Asp Asp Phe Val Gly Ala Leu
                660                 665                 670

Ile Phe Ser Gly Ala Val Ile Leu Leu Glu Phe Ile Pro Glu Ile Ala
                675                 680                 685

Ile Pro Val Leu Gly Thr Phe Ala Leu Val Ser Tyr Ile Ala Asn Lys
                690                 695                 700

Val Leu Thr Val Gln Thr Ile Asp Asn Ala Leu Ser Lys Arg Asn Glu
705                 710                 715                 720
```

-continued

Lys Trp Asp Glu Val Tyr Lys Tyr Ile Val Thr Asn Trp Leu Ala Lys
                    725                 730                 735

Val Asn Thr Gln Ile Asp Leu Ile Arg Lys Lys Met Lys Glu Ala Leu
                740                 745                 750

Glu Asn Gln Ala Glu Ala Thr Lys Ala Ile Ile Asn Tyr Gln Tyr Asn
                755                 760                 765

Gln Tyr Thr Glu Glu Lys Asn Asn Ile Asn Phe Asn Ile Asp Asp
            770                 775                 780

Leu Ser Ser Lys Leu Asn Glu Ser Ile Asn Lys Ala Met Ile Asn Ile
785                 790                 795                 800

Asn Lys Phe Leu Asn Gln Cys Ser Val Ser Tyr Leu Met Asn Ser Met
                805                 810                 815

Ile Pro Tyr Gly Val Lys Arg Leu Glu Asp Phe Asp Ala Ser Leu Lys
                820                 825                 830

Asp Ala Leu Leu Lys Tyr Ile Tyr Asp Asn Arg Gly Thr Leu Ile Gly
                835                 840                 845

Gln Val Asp Arg Leu Lys Asp Lys Val Asn Asn Thr Leu Ser Thr Asp
                850                 855                 860

Ile Pro Phe Gln Leu Ser Lys Tyr Val Asp Asn Gln Arg Leu Leu Ser
865                 870                 875                 880

Thr Phe Thr Glu Tyr Ile Lys Asn Ile Ile Asn Thr Ser Ile Leu Asn
                885                 890                 895

Leu Arg Tyr Glu Ser Asn His Leu Ile Asp Leu Ser Arg Tyr Ala Ser
                900                 905                 910

Lys Ile Asn Ile Gly Ser Lys Val Asn Phe Asp Pro Ile Asp Lys Asn
                915                 920                 925

Gln Ile Gln Leu Phe Asn Leu Glu Ser Ser Lys Ile Glu Val Ile Leu
                930                 935                 940

Lys Asn Ala Ile Val Tyr Asn Ser Met Tyr Glu Asn Phe Ser Thr Ser
945                 950                 955                 960

Phe Trp Ile Arg Ile Pro Lys Tyr Phe Asn Ser Ile Ser Leu Asn Asn
                965                 970                 975

Glu Tyr Thr Ile Ile Asn Cys Met Glu Asn Asn Ser Gly Trp Lys Val
                980                 985                 990

Ser Leu Asn Tyr Gly Glu Ile Ile Trp Thr Leu Gln Asp Thr Gln Glu
                995                 1000                1005

Ile Lys Gln Arg Val Val Phe Lys Tyr Ser Gln Met Ile Asn Ile
    1010                1015                1020

Ser Asp Tyr Ile Asn Arg Trp Ile Phe Val Thr Ile Thr Asn Asn
    1025                1030                1035

Arg Leu Asn Asn Ser Lys Ile Tyr Ile Asn Gly Arg Leu Ile Asp
    1040                1045                1050

Gln Lys Pro Ile Ser Asn Leu Gly Asn Ile His Ala Ser Asn Asn
    1055                1060                1065

Ile Met Phe Lys Leu Asp Gly Cys Arg Asp Thr His Arg Tyr Ile
    1070                1075                1080

Trp Ile Lys Tyr Phe Asn Leu Phe Asp Lys Glu Leu Asn Glu Lys
    1085                1090                1095

Glu Ile Lys Asp Leu Tyr Asp Asn Gln Ser Asn Ser Gly Ile Leu
    1100                1105                1110

Lys Asp Phe Trp Gly Asp Tyr Leu Gln Tyr Asp Lys Pro Tyr Tyr
    1115                1120                1125

-continued

| | | | | | | | | | | | |
|---|---|---|---|---|---|---|---|---|---|---|---|
| Met | Leu<br>1130 | Asn | Leu | Tyr | Asp<br>1135 | Pro | Asn | Lys | Tyr | Val<br>1140 | Asp | Val | Asn | Asn |
| Val | Gly<br>1145 | Ile | Arg | Gly | Tyr<br>1150 | Met | Tyr | Leu | Lys | Gly<br>1155 | Pro | Arg | Gly | Ser |
| Val | Met<br>1160 | Thr | Thr | Asn | Ile<br>1165 | Tyr | Leu | Asn | Ser | Ser<br>1170 | Leu | Tyr | Arg | Gly |
| Thr | Lys<br>1175 | Phe | Ile | Ile | Lys<br>1180 | Lys | Tyr | Ala | Ser | Gly<br>1185 | Asn | Lys | Asp | Asn |
| Ile | Val<br>1190 | Arg | Asn | Asn | Asp<br>1195 | Arg | Val | Tyr | Ile | Asn<br>1200 | Val | Val | Val | Lys |
| Asn | Lys<br>1205 | Glu | Tyr | Arg | Leu<br>1210 | Ala | Thr | Asn | Ala | Ser<br>1215 | Gln | Ala | Gly | Val |
| Glu | Lys<br>1220 | Ile | Leu | Ser | Ala<br>1225 | Leu | Glu | Ile | Pro | Asp<br>1230 | Val | Gly | Asn | Leu |
| Ser | Gln<br>1235 | Val | Val | Val | Met<br>1240 | Lys | Ser | Lys | Asn | Asp<br>1245 | Gln | Gly | Ile | Thr |
| Asn | Lys<br>1250 | Cys | Lys | Met | Asn<br>1255 | Leu | Gln | Asp | Asn | Asn<br>1260 | Gly | Asn | Asp | Ile |
| Gly | Phe<br>1265 | Ile | Gly | Phe | His<br>1270 | Gln | Phe | Asn | Asn | Ile<br>1275 | Ala | Lys | Leu | Val |
| Ala | Ser<br>1280 | Asn | Trp | Tyr | Asn<br>1285 | Arg | Gln | Ile | Glu | Arg<br>1290 | Ser | Ser | Arg | Thr |
| Leu | Gly<br>1295 | Cys | Ser | Trp | Glu<br>1300 | Phe | Ile | Pro | Val | Asp<br>1305 | Asp | Gly | Trp | Gly |
| Glu | Arg<br>1310 | Pro | Leu | | | | | | | | | | | |

The invention claimed is:

1. A pharmaceutical composition comprising a modified botulinum toxin, the modified botulinum toxin comprising a natural heavy chain and a modified light chain, wherein the light chain comprises at least one and at most 20 amino acid residues occurring naturally at its N-terminus being mutated to a cysteine residue, and at least one chain of PEG coupled to at least one cysteine residue in said 20 amino acid residues at said N-terminus.

2. The pharmaceutical composition according to claim 1, wherein the composition is stabilized without addition of human serum albumin (HSA).

3. The pharmaceutical composition according to claim 1, wherein the composition is in lyophilized form.

4. The pharmaceutical composition according to claim 1, wherein the composition is in liquid form.

5. The pharmaceutical composition according to claim 1, wherein the composition is formulated for intramuscular injection.

6. The pharmaceutical composition according to claim 2, wherein the composition is in lyophilized form.

7. The pharmaceutical composition according to claim 2, wherein the composition is in liquid form.

8. The pharmaceutical composition according to claim 2, wherein the composition is formulated for intramuscular injection.

* * * * *